(12) United States Patent
Cimini et al.

(10) Patent No.: US 6,462,251 B1
(45) Date of Patent: Oct. 8, 2002

(54) MECHANICALLY STRAINABLE COMPOSITE LAMINATED STRUCTURE

(75) Inventors: Carmine Cimini, Pescara (IT); Guido Bonelli, Pescara (IT); Giovanni Carlucci, Chieti (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/762,747

(22) PCT Filed: Aug. 11, 1999

(86) PCT No.: PCT/US99/18253

§ 371 (c)(1),
(2), (4) Date: Feb. 12, 2001

(87) PCT Pub. No.: WO00/09325

PCT Pub. Date: Feb. 24, 2000

(30) Foreign Application Priority Data

Aug. 12, 1998 (EP) ............................................. 98115154

(51) Int. Cl.$^7$ ................................................. A61F 13/15
(52) U.S. Cl. .................... 604/358; 156/60; 604/385.01; 604/385.24; 604/385.16; 604/385.22
(58) Field of Search .......................... 604/358, 385.04, 604/385.01, 385.24, 385.16, 385.22; 156/60; 428/100

(56) References Cited

U.S. PATENT DOCUMENTS

| 5,092,862 A | * | 3/1992 | Muckenfuhs et al. | .. 604/385.02 |
| 5,605,735 A | * | 2/1997 | Zehner et al. | .............. 428/100 |
| 6,264,641 B1 | * | 7/2001 | Van Gompel et al. | .. 604/385.22 |

FOREIGN PATENT DOCUMENTS

| EP | 0 707 841 A1 | 4/1996 |
| EP | 0 710 470 A1 | 5/1996 |
| WO | WO 97/12576 A1 | 4/1997 |
| WO | WO 00/09325 A1 | 2/2000 |

* cited by examiner

*Primary Examiner*—A. Vanatta
*Assistant Examiner*—Angela J. Grayson
(74) *Attorney, Agent, or Firm*—Theodore P. Cummings; Kevin C. Johnson

(57) ABSTRACT

The present invention relates to a composite laminated structure comprising a substrate and an apertured layer joined together by means of a layer of an adhesive composition. The laminated structure is made extensible in designated zones by mechanical straining and the adhesive composition provides both an effective connection of the layers forming the composite laminated structure and an improved processability of the laminated structure by mechanical straining. The composite laminated structure preferably constitutes side flaps in a disposable absorbent article such as a sanitary napkin.

11 Claims, 2 Drawing Sheets

MECHANICALLY STRAINABLE COMPOSITE LAMINATED STRUCTURE

FIELD OF THE INVENTION

The present invention relates to a composite laminated structure comprising a substrate and an apertured layer joined together by means of a layer of an adhesive composition. The laminated structure is made extensible in designated zones by mechanical straining and preferably constitutes side flaps in a disposable absorbent article such as a sanitary napkin.

BACKGROUND OF THE INVENTION

Absorbent articles such as sanitary napkins, pantiliners, and incontinence pads are devices that are typically worn in the crotch region of an undergarment. These devices are designed to absorb and retain liquid and other discharges from the human body and to prevent body and clothing soiling. Sanitary napkins are a type of absorbent article worn by women in a pair of panties and is normally positioned between the wearer's legs, adjacent to the perineal area of the body. Sanitary napkins in particular with side wrapping elements, often also referred to as side flaps or wings, are disclosed in the literature and are available in the marketplace.

Sanitary napkins having wings or side flaps of various types are disclosed in U.S. Pat. Nos. 4,687,478, 4,608,047, 4,589,876, Reexamination B1 4,589,876, 4,285,343. Sanitary napkins having wings are commonly viewed as providing good protection against soiling.

However, some women find applying sanitary napkins having side flaps to be inconvenient for various reasons. For instance, some women find it to be difficult to attach the side flaps to the underside of the crotch of their panties. This can be due to factors such as difficulties in folding the side flaps properly into place and to stick them to the undergarment As a result, some women still prefer a sanitary napkin without side flaps. In addition, some women who generally prefer a sanitary napkin with side flaps, occasionally (such as during periods of light flow) prefer a sanitary napkin without. Therefore, there is a need for a sanitary napkin which provides an alternative to sanitary napkins having conventional side flaps while still providing a similar protection.

Several variations of sanitary napkins having conventional side flaps have been suggested. For example, U.S. Pat. No. 4,911,701 discloses a sanitary napkin having elastic strands for providing a greater convex shape to the body-facing portion of the central absorbent and for enabling adhesive-free placement of the side flaps into the panties. U.S. Pat. No. 4,940,462 discloses a sanitary napkin with longitudinally expandable flaps. The flaps are designed to fold over the exterior of the wearer's panty and then to expand to conform with the contour of the panties. Further improvements of side wrapping elements with extensible zones have been disclosed in U.S. application Ser. No. 08/124,180 of Sep. 17, 1993; and Ser. No. 08/277,733 of Jul. 20, 1994 and European application 94202252.6 of Aug. 3, 1994.

In these disclosures the extensibility can be provided by a number of different processes. For example the extensible zones can be created by mechanically straining, corrugating, "ring-rolling", heating and deforming, subjecting portions of the side wrapping elements or flaps to compression between mating plates, and the like.

In particular high speed mechanical straining such as corrugating or ring-rolling are desirable due to the manufacturing efficiency from allowing high speed production. Also ring-rolled zones of extensibility can have an angled extensibility relative to the machine direction (process transport direction). Suitable methods for ring-rolling, typically by means of two rolls of meshed interlocking teeth and grooves, are described in U.S. Pat. Nos. 4,107,364, 4,834, 741, 5,143,679, 5,156,793 and 5,167,897.

Particularly preferred side wrapping elements or flaps comprise at least two layers of material but sometimes more, for example four layers of materials which are joined together forming a composite laminated structure that is rendered extensible only after being formed into a laminate. In particular prior art sanitary napkins with side wrapping elements having extensible zones are constructed such that the side wrapping elements are formed by laterally extending parts of the uppermost layer of the sanitary napkin (typically called topsheet) and the lowermost layer of the sanitary napkin (typically designated the backsheet).

The laminate formed in the area laterally outside the main portion of the sanitary napkin is strained by mechanical processes like the aforementioned ring-rolling at the production speed of these articles. For the laminate to display uniform behaviour during the mechanical straining the individual layers need to be properly joined to each other at least in the areas of mechanical straining.

Typically adhesives, especially hot melt adhesives have been suggested and used for that purpose. A large variety of adhesives for the different situations occurring in the manufacturing process of disposable absorbent articles have been developed and continue to be developed. Alternative joining methods include welding which is used between plastic materials of similar kinds allowing to create areas were the materials are fused to each other to create permanent connections, or crimping which is a local mechanical deformation of the layers such that the layers interlock locally.

A problem encountered when applying mechanical strain, for example by means of a ring rolling process, to a composite laminated structure comprising an apertured layer joined by means of an adhesive to a substrate, in order to provide designated zones of the structure with extensibility, is that machinery parts, typically the apexes of the metal teeth of one of the rolls used in the ring rolling process, come into direct contact with the adhesive layer through the apertures of the apertured layer. The apertured layer can be a nonwoven or, preferably, an apertured three dimensional polymeric film, constituting e.g. the topsheet of a sanitary napkin, and the substrate can be a liquid impermeable polymeric film, preferably a liquid impermeable, moisture vapour permeable layer, such as a microporous breathable film, comprised in a preferably breathable backsheet.

Adhesives used in the field of disposable absorbent articles are tackified to display adhesive characteristics over a broad range of temperatures. They are usually still tacky at room temperature and therefore during the mechanical straining step by means of e.g. ring rolling they can still stick to the teeth of a roll for ring rolling through the apertures of the apertured layer.

It is particularly undesirable during the straining process to have exposed adhesive on the outside of any of the laminates because adhesive build up, in particular sticky adhesive build up on fast moving machinery parts quickly leads to unstable process conditions. As a minimum the occurrence of these conditions require frequent cleaning but can even cause disastrous material destruction leading to machine stops and reduce efficiency. Particularly, when a ring rolling process is performed and one of the layers of the laminated structure has apertures the adhesive that sticks to the apexes of the teeth of one of the rolls can pull the portions of the layer joined to the apertured layer, i.e. the substrate, through the apertures of the apertured layer, to the extent that ruptures and pin holes are created in this substrate. This is detrimental to the integrity of the structure, and also to the liquid imperviousness of the substrate, when, as it is preferred, it constitutes at least part of a backsheet structure in a disposable absorbent article, and therefore ruptures in the substrate ultimately can cause liquid leakage during the use of the product.

This pulling action is even more effective in case of a composite laminated structure comprising a three dimensional apertured thermoplastic polymeric film as the apertured layer and a microporous breathable film as the substrate, since the presence of the micropores in the microporous film makes the film somewhat weaker and more subject to ruptures under the pulling action of the adhesive stuck e.g. to the teeth of a roll for ring rolling.

Adhesive which may be exposed through the apertures of an apertured layer on the outside of a composite laminated structure in a disposable absorbent articles is also highly undesirable for the consumer. If adhesives which are tacky at the usage temperature of these products contact the wearer's skin or garment they will usually cause residue adhesive on garments or irritation to the wearer's skin.

These undesirable effects can be also enhanced by the mechanical straining itself, e.g. a ring rolling process of a laminated structure comprising a three dimensional apertured film joined to a substrate, e.g. a microporous breathable film, since the mechanical strain induced by the ring rolling increases the size of the apertures in the three dimensional apertured film, and at the same time at least partially destroys the three dimensional structure of the apertured film itself, so reducing its thickness. This means that the adhesive is exposed through enlarged apertures on the outside of such a laminate, and is also closer to the external surface, and therefore is more likely to come in contact e.g. with the wearer's skin or garment.

It has been found that an alternative method of joining the materials of a composite laminated structure, which is called soldering, can be used in the process of mechanical straining of the laminated structure. This method as such is known from the art of joining metals, but has been also been applied in the field of disposable absorbent articles, as described in patent applications EP-A-707841 and EP-A-710470. A solder, as described in the cited application, is an adhesive which shows adhesive behaviour when it is applied at its process temperature, but is not sticky at room temperature. Therefore during the mechanical straining step, e.g. by means of ring rolling, of a composite laminated structure comprising a substrate joined to an apertured layer by means of the solder, the adhesive used as the solder cannot stick to the machine parts, and to anything else during the subsequent use of the laminate, as far as the solder (adhesive) is kept at room temperature.

A problem with composite laminated structures comprising an apertured layer joined to a substrate by means of known adhesives used as solders is that such adhesives, while being not sticky at room temperature, and therefore capable of avoiding both the adhesive build up onto the machinery parts, and consequent damages to the laminated structure due to adhesion between the laminated structure itself and the machinery parts onto which the adhesive can stick, and possible stickiness of the laminated structure during the use of the structure itself, for example in a disposable absorbent product, do not have sufficient extensibility to withstand the mechanical straining process.

Known adhesives used as solders in such laminated structures for their preferred behaviour in terms of no stickiness at room temperature have a relatively high hardness and a low elongation at break, and therefore make the composite laminated structure stiff. This causes the adhesive layer joining the layers of the composite laminated structure to break into small pieces when the laminated structure is subjected to mechanical straining, e.g. by means of ring rolling, to be provided with extensibility in designated zones. The joining between the layers of the composite laminated structure can therefore fail and cause delamination of the structure, i.e. separation of the layers over at least part of the joined area.

It is therefore an object of the present invention to provide a composite laminated structure comprising a substrate and an apertured layer joined together by means of an adhesive layer which, while avoiding the problems related to the exposure of the adhesive outside of the structure, e.g. direct contact of the adhesive with machinery parts through the apertures of the apertured layer, also achieves a secure joining of the layers when the structure is mechanically strained in order to be provided with designated zones of extensibility.

It is another object of the present invention to provide a disposable absorbent article comprising the composite laminated structure having extensible zones, wherein the substrate is a liquid impervious, preferably moisture vapour permeable backsheet, and the apertured layer is a liquid permeable topsheet. Preferably the absorbent article is a sanitary napkin with side flaps, and the flaps comprise the composite laminated structure having zones of extensibility to facilitate folding of the flaps.

SUMMARY OF THE INVENTION

A composite laminated structure comprising a substrate, an apertured layer bonded to the substrate, and a layer of an adhesive composition comprised therebetween and adhesively joining the substrate and the apertured layer. The composite laminated structure has designated zones rendered extensible by mechanical straining.

The adhesive composition has a peel force on steel at a temperature of 23° C. of less than 10 g according to the Peel Force on Steel Test described herein, and the adhesive composition has an elongation at break of at least 35% according to ASTM D 638M-91a where the sample thickness is 4 mm.

The composite laminated structure of the present invention is preferably comprised in a disposable absorbent article, preferably a sanitary napkin. The mechanical straining is preferably provided by ring rolling according to the above identified prior art references.

DETAILED DESCRIPTION OF THE INVENTION

Figure 1:
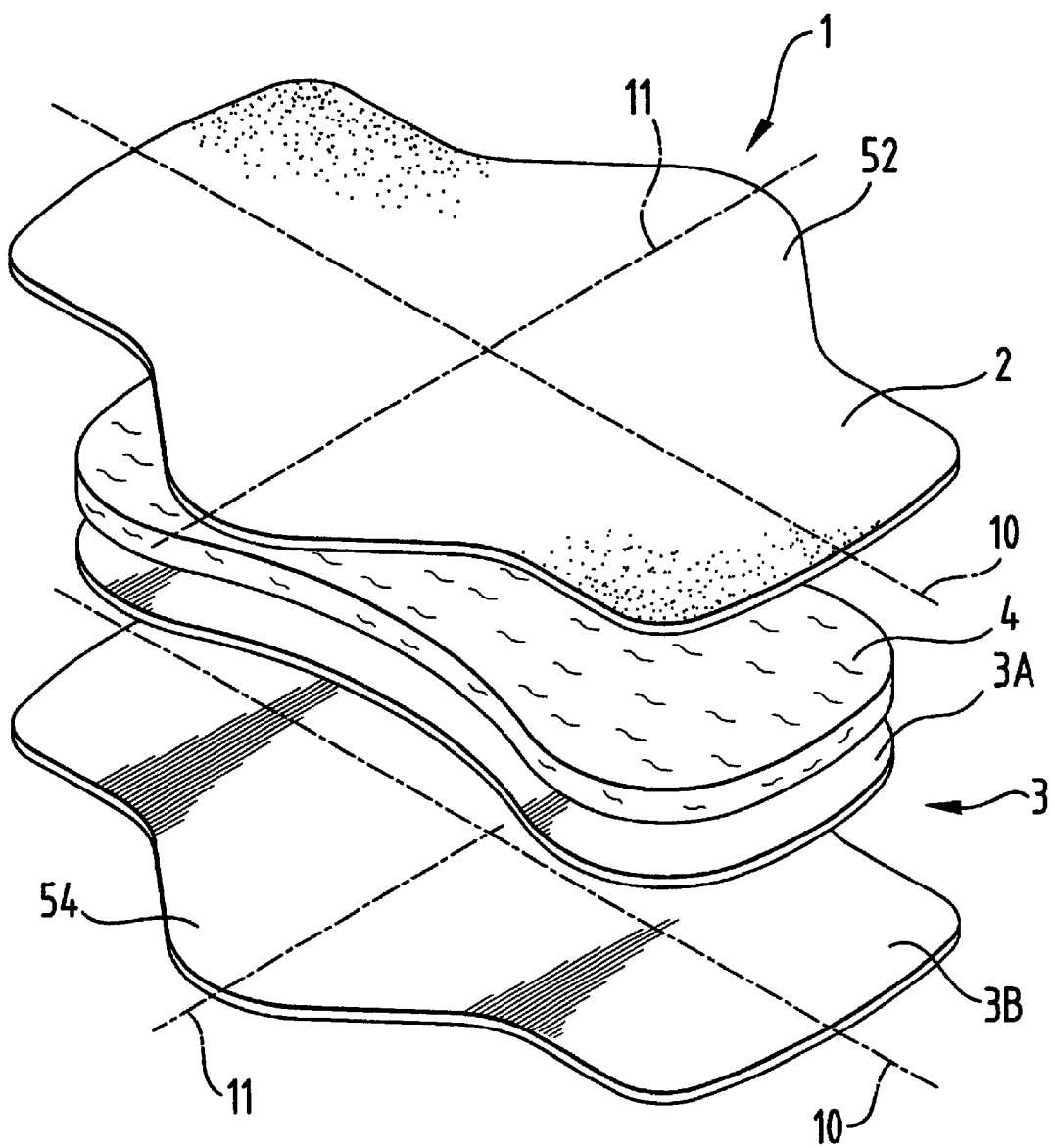
FIG. 1 is an exploded view of a sanitary napkin having side flaps and comprising a composite laminated structure made according to the present invention.
Figure 2:
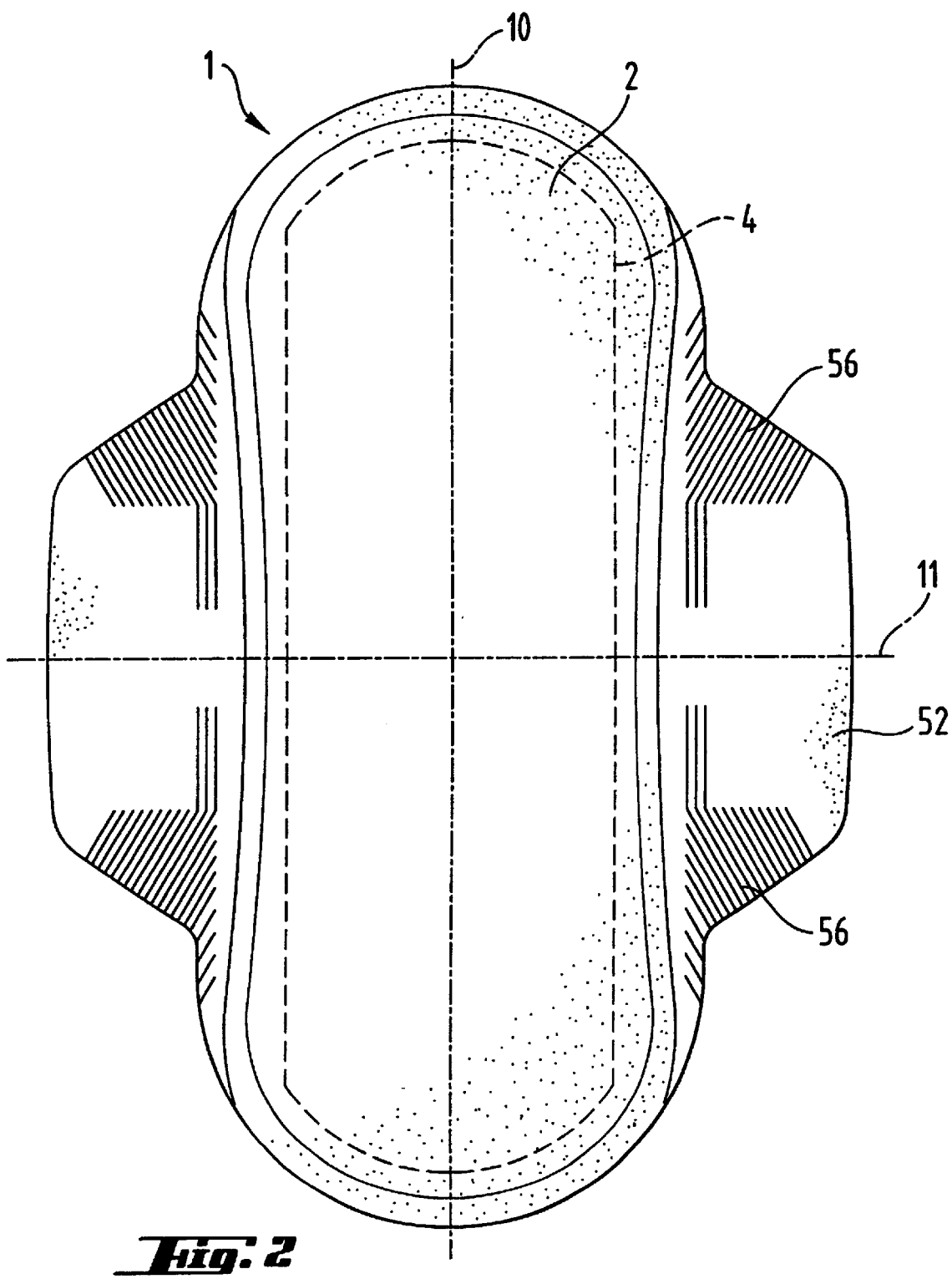
FIG. 2 shows a top plan view of a sanitary napkin having ring rolled zones of extensibility in the side flaps. The zones are indicated by hatched lines symbolizing that they are angled to the longitudinal axis.

According to the present invention a composite laminated structure is provided which comprises a substrate, an apertured layer and a layer of adhesive joining the apertured layer and the substrate; the laminated structure has extensible zones provided by means of mechanical straining. The composite laminated structure is preferably used in a disposable absorbent article such as a sanitary napkin having side flaps, as illustrated in FIGS. 1 and 2, the flaps comprising the laminated structure of the invention.

The absorbent article has a body facing surface, typically provided by a liquid impermeable layer of fibrous or film like structure; a garment facing surface, preferably provided by a liquid impermeable, but breathable layer and an absorbent structure placed between the body facing surface and the garment facing surface. The absorbent article has a longitudinal axis 10 and a lateral axis 11 as shown in the Figures and can comprise any of the components or features usual in the art including in particular side flap components and any sort of extensibility or elastication feature known in the art.

The preferred sanitary napkin or panty liner made according to the present invention has a pair of side wrapping elements (or "undergarment covering components") that provide coverage to the wearer's panties to reduce side soiling (i.e., staining of the edges of the panty crotch) without the use of conventional flaps.

The preferred sanitary napkin or panty liner comprises a main body portion comprising a liquid pervious topsheet, a liquid impervious backsheet joined to the topsheet, and an absorbent core positioned between the topsheet and the backsheet. The side wrapping elements are either integrally formed with the main body portion which is preferred or joined to the garment-facing side of the main body portion inboard of the longitudinal side edges thereof.

In the preferred embodiment of the present invention illustrated in FIGS. 1 and 2 the side wrapping elements of the sanitary napkin comprise the composite laminated structure of the present invention, formed by the topsheet as the apertured layer and by the backsheet as the substrate both extending laterally of the main body portion of the article, outboard of the longitudinal side edges thereof, and being joined by a layer of adhesive not shown in FIG. 1.

The composite laminated structure in each of the side wrapping elements is provided with at least one zone of extensibility, preferably two spaced apart zones of extensibility 56 as shown in FIG. 2, which are symmetrically placed in respect to the longitudinal centerline of the absorbent article. The zones of extensibility are regions of the composite laminated structure in the side wrapping elements that have a greater range of extension than the adjacent regions of the composite laminated structure.

The disposable article for absorbing liquid is described below by reference to a sanitary napkin or panty liner. However products such as adult or baby diapers or adult incontinence inserts comprising zones of extensibility can similarly benefit from the composite laminated structure of the present invention.

If the side wrapping elements are formed integrally with the main body portion of the absorbent article, as it is preferred, notch regions are formed extending around the intersection between the perimeter of the side wrapping elements and the longitudinal side edge of the main body portion where the side wrapping elements extend beyond the longitudinal side edge of the main body portion. For these integral side wrapping element designs it is preferable when at least one symmetric pair of zones of extensibility extend into said notch regions, i.e. each extensible zone extends across the longitudinal side edge of the main body portion.

Alternatively for side wrapping elements which are provided as separate elements and which are attached to said garment-facing side (and which are unattached outward from where they are attached) the distance between the laterally most inward points of the zones of extensibility and the longitudinal centerline is preferably in the range of 40 mm to 50 mm.

Generally the zone of extensibility can be primarily extensible in the longitudinal direction or primarily in the transverse direction or in any direction falling therebetween. For integrally formed side wrapping elements the zone of extensibility is most preferably extensible in a direction following as close as possible the adjacent outer perimeter of the absorbent article. Preferably the zones of extensibility are provided with corrugations having fold lines.

The sanitary napkins of the present invention provide an alternative to conventional sanitary napkins having side flaps. In one embodiment the side wrapping elements require no action on the part of the wearer to fold them under her panties or to attach them to the panties. The side wrapping elements stay in place well enough to cover the sides edges of the wearer's panties without affixing them underneath the wearer's panties.

In an alternative embodiment, particularly for side wrapping elements extending far outside the main body portion, the sanitary napkin may be provided with a fastener, such as a pressure sensitive adhesive. The adhesive fastener may be provided on the garment-facing side of the main body portion and also extend onto the garment-facing side of the side wrapping elements. In this embodiment, particularly in narrow panty crotches, the side wrapping elements may fold around the side edge of the wearer's panty crotch so that portions of the side wrapping elements even overlap. This forms a novel structure that pinches the side edge of the panties between the folded portion of the side wrapping elements.

Topsheet

The topsheet 2 is compliant, soft feeling, and non-irritating to the wearer's skin. The topsheet also can have elastic characteristics allowing it to be stretched in one or two directions in portions of the topsheet or throughout its extension. Further, the topsheet is fluid pervious permitting fluids (e.g., menses and/or urine) to readily penetrate through its thickness. A suitable topsheet can be manufactured from a wide range of materials such as woven and non woven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Preferred topsheets for use in the present invention are selected from high loft nonwoven topsheets and apertured formed film topsheets. Apertured formed films are especially preferred for the topsheet because they are pervious to body exudates and yet non absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. Nos. 3,929,135; 4,324,246; 4,342,314; 4,463,045; and 5,006,394. Particularly preferred microapetured formed film topsheets are disclosed in U.S. Pat. Nos. 4,609,518 and 4,629,643. A preferred topsheet for the present invention comprises the formed film described in one or more of the above patents and marketed on sanitary napkins by The Procter & Gamble Company of Cincinnati, Oh. as "DRI-WEAVE".

Topsheets having not a homogeneous distribution of liquid passage ways but only a portion of the topsheet comprising liquid passage ways are also contemplated by the present invention. Typically such topsheets would have the liquid passage ways oriented such that they result in a centrally permeable and peripherally impermeable topsheet for liquids.

The body surface of the formed film topsheet can be hydrophilic so as to help liquid to transfer though the topsheet faster than if the body surface was not hydrophilic. In a preferred embodiment, surfactant is incorporated into the polymeric materials of the formed film topsheet such as is described in PCT publication WO 93/09741. Alternatively, the body surface of the topsheet can be made hydrophilic by treating it with a surfactant such as is described in U.S. Pat. No. 4,950,254.

Another alternative are so called hybrid topsheets which incorporate fibrous and film like structures particularly useful embodiments of such hybrid topsheets are disclosed in PCT publications WO 93/09744; WO 93/11725 or WO 93/11726.

In the preferred embodiment of the present invention the topsheet 2 comprises a three dimensional apertured thermoplastic film and typically extends across the whole of the absorbent structure 4 and outside the area coextensive with the absorbent structure 4. As indicated in FIG. 1 the topsheet 2 extends and forms all of the preferred side flaps as shown and designated 52 in FIG. 1, and constitutes the apertured layer of the composite laminated structure of the present invention.

When referring to the topsheet a multi layer structure or a mono layer structure are also contemplated. If the various layers of multilayer topsheets are joined to each other they are as such also susceptible to form a composite laminated structure having designated zones of extensibility provided by means of mechanical straining.

The hybrid topsheet mentioned above is such a multi layer design but other multilayer topsheets such as primary and secondary topsheet designs are also considered susceptible to form a composite laminated structure according to the present invention.

Absorbent Structure

The absorbent structure is shown as a single entity 4 in FIG. 1. It can include the following components: (a) optionally a primary fluid distribution layer preferably together with a secondary fluid distribution layer; (b) a fluid storage layer; (c) optionally a fibrous ("dusting") layer underlying the storage layer; and (d) other optional components.

a) Primary/Secondary Fluid Distribution Layer

One optional component of the absorbent structure according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilised.

b) Fluid Storage Layer

Positioned in fluid communication with, and typically underlying the primary or secondary distribution layers, is a fluid storage layer. The fluid storage layer can comprise any usual absorbent material or combinations thereof. It preferably comprises absorbent gelling materials usually referred to as "hydrogel", "superabsorbent", "hydrocolloid" materials in combination with suitable carriers.

The absorbent gelling materials are capable of absorbing large quantities of aqueous body fluids, and are further capable of retaining such absorbed fluids under moderate pressures. The absorbent gelling materials can be dispersed homogeneously or non-homogeneously in a suitable carrier. The suitable carriers, provided they are absorbent as such, can also be used alone.

Suitable absorbent gelling materials for use herein will most often comprise a substantially water-insoluble, slightly cross linked, partially neutralised, polymeric gelling material. This material forms a hydrogel upon contact with water. Such polymer materials can be prepared from polymerizable, unsaturated, acid-containing monomers. Suitable unsaturated acidic monomers for use in preparing the polymeric absorbent gelling material used in this invention include those listed in U.S. Pat. No. 4,654,039 reissued as RE 32,649. Preferred monomers include acrylic acid, methacrylic acid, and 2-acrylamido-2-methyl propane sulfonic acid. Acrylic acid itself is especially preferred for preparation of the polymeric gelling material.

Suitable carriers include materials which are conventionally utilised in absorbent structures such as cellulose fibers, in the form of fluff and/or tissues. Suitable carriers can be used together with the absorbent gelling material, however they can also be used alone or in combinations. Most preferred are tissue or tissue laminates in the context of sanitary napkins/party liners.

In an embodiment made according to the present invention the absorbent structure 4 comprises a double layer tissue laminate formed by folding the tissue onto itself.

Modified cellulose fibers such as the stiffened cellulose fibers can also be used. Synthetic fibers can also be used and include those made of cellulose acetate, polyvinyl fluoride, polyvinylidene chloride, acrylics (such as Orion), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., that lower rewet problems.

If the absorbent gelling material is dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing absorbent gelling materials partially or fully.

c) Optional Fibrous ("Dusting") Layer

An optional component for inclusion in the absorbent structure according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent structure. Indeed, in those instances where the absorbent gelling material is in the form of macro structures such as fibbers, sheets or strips, this fibrous "dusting" layer need not be included. However, this "dusting" layer provides some additional fluid-handling capabilities such as rapid wicking of fluid along the length of the pad.

d) Other Optional Components of the Absorbent Structure

The absorbent structure according to the present invention can include other optional components normally present in absorbent webs. For example, a reinforcing scrim can be positioned within the respective layers, or between the respective layers, of the absorbent structure. Such reinforcing scrims should be of such configuration as to not form interfacial barriers to fluid transfer, especially if positioned between the respective layers of the absorbent structure. Given the structural integrity that usually occurs as a result of thermal bonding, reinforcing scrims are usually not required for the absorbent structures according to the present invention.

Another component which can be included in the absorbent structure according to the invention and preferably is provided close to or as part of the primary or secondary fluid distribution layer are odor control agents. Typically active carbon coated with or in addition to other odor control agents, in particular suitable zeolite or clay materials, are optionally incorporated in the absorbent structure. These components can be incorporated in any desired form but often are included as discrete particles.

Backsheet

The backsheet 3 primarily prevents the exudates absorbed and contained in the absorbent structure from wetting articles that contact the absorbent product such as underpants, pants, pyjamas and undergarments. The backsheet 3 is preferably impervious to liquids (e.g., menses and/or urine) and can be manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions.

In the preferred embodiment of the present invention illustrated in FIGS. 1 and 2, the backsheet 3 comprises two layers: a first layer comprising a gas permeable apertured formed film layer 3A and a second layer comprising a breathable microporous film layer 3B.

Preferably the apertured formed film of the first layer 3A comprises a layer having discrete apertures which extend beyond the horizontal plane of the garment facing surface of the layer towards the absorbent core 4 thereby forming protuberances. Each protuberance has an orifice located at its terminating end. Preferably the protuberances have a funnel or conical shape, similar to those described in U.S. Pat. No. 3,929,135. The apertures located within the plane of the layer and the orifices located at the terminating end of protuberances themselves maybe circular or non circular. In any case the cross sectional dimension or area of the orifice at the termination of the protuberance is smaller than the cross sectional dimension or area of the aperture located within the plane of the layer. The first layer 3A of the backsheet 3 may be made of any material known in the art, but is preferably manufactured from commonly available polymeric materials. The first layer 3A may also comprise any type of formed films which may be used for a topsheet as described above.

The second layer 3B of the backsheet 3 preferably comprises a breathable microporous film composed of a thermoplastic resin and inorganic fillers dispersed in the thermoplastic resin. Suitable thermoplastic polymers include polyolefins such as polyethylenes, including linear low density polyethylene (LLDPE), low density polyethylene (LDPE), ultra low density polyethylene (ULDPE), high density polyethylene (HDPE), or polypropylene and blends thereof with the above and other materials. Examples of other suitable thermoplastic polymers which may also be used include, but are not limited to, polyester, polyurethanes, compostable or biodegradable polymers, thermoplastic elastomers, and metallocene catalyst-based polymers (e.g., INSITE® available from Dow Chemical Company and Exxact® available from Exxon). The inorganic material or filler can comprise talc, silica, calcium carbonate, clay, titanium dioxide, barium sulfate, with the preferred inorganic filler being calcium carbonate. The inorganic filler may be coated with fatty acid esters, fatty acids or their metal salts to improve the dispersion of the filler particles into the thermoplastic polymer and to obtain higher loadings in the polymer. The inorganic filler and the thermoplastic polymer are blended together to form a homogeneous mixture in a suitable mixing extruder, or in a separate preliminary compounding step. The mixture is then cast or blown into a film. The obtained film is stretched at least in one direction to impart breathability on the substantially entire area of the film. The step of stretching a film to impart breathability may be done at a different place prior to manufacturing process of absorbent articles. Alternatively, the step of stretching may be done at the same place, i.e., same manufacturing process, prior to assembling a breathable microporous film with other elements of absorbent articles. In any case, the film is imparted breathability on the substantially entire area of the film before the resulting breathable microporous film is assembled with other elements of absorbent articles.

The topsheet, the backsheet, and the absorbent core may be assembled in a variety of configurations known in the art (including layered or "sandwich" configurations and wrapped or "tube" configurations). FIGS. 1 and 2 show a preferred embodiment of the sanitary napkin 1 assembled in a sandwich construction in which the topsheet 2 and the breathable microporous film 3B have length and width dimensions generally larger than those of the absorbent core 4. The topsheet 2 and the breathable microporous film 3B extend beyond the edges of the absorbent core 4 to form portions of the periphery.

The sanitary napkin 1 shown in FIGS. 1 and 2 also comprises a pair of flaps 52 that are joined to the main body portion along a juncture. The flaps 52 extend laterally outward beyond the longitudinal side edges of the main body portion from their proximal edges to their distal edges (or "free ends"). The flaps 52 comprise a flap topsheet and a flap backsheet. In the embodiment shown in FIGS. 1 and 2, the flaps 52 are integral with the main body portion, that is, the flap topsheet and the flap backsheet comprise integral extensions of the topsheet 2 and of the breathable microporous film 3B, respectively.

The apertured formed film 3A of the backsheet has approximately the same shape as the absorbent core 4 to cover at least the region where the absorbent core 4 lies as shown in FIG. 1. Alternatively, it may have a little bigger shape than the absorbent core 4, or may have the same shape as the main body portion of the sanitary napkin 1. In any case, preferably, the apertured formed film 3A does not extend into the flaps 52 as shown in FIG. 1. Alternatively, but less preferably, the apertured formed film 3A may extend into the flaps 52 so that the apertured formed film constitutes a part of the flaps 52.

The topsheet 2 and the breathable microporous film 3B can be joined in any suitable manner known in the art for this purpose. Preferably, in the embodiment shown, these portions of the topsheet 2 and of the breathable microporous film 3B are joined using adhesives over substantially the entire portions that extend beyond the edges of the absorbent core 4, and therefore over the entire region of the flaps 52.

In the embodiment shown in FIG. 1, the first layer 3A is typically located adjacent to the absorbent core 4 and the subsequent layer 3B of the backsheet is typically located further away from the absorbent core 4. The backsheet 3 may also comprise additional layers. All of the layers of the backsheet 3 can be substantially in intimate and direct contact with one another.

The function of flaps, also called side wrapping elements, whether integral or joined to the article after being formed separately, is further improved by rendering them extensible in one or both directions parallel to the longitudinal axis 10 or lateral axis 11. The extensibility can be provided across all or only part of the side wrapping elements and can be achieved by pleating or ring-rolling those parts which are to be rendered extensible.

The layered structure formed by the topsheet 2 (apertured layer) and by the breathable microporous film 3B (substrate) of the backsheet extending beyond the longitudinal edges of the absorbent article to form side flaps 52, also comprising the adhesive layer joining the apertured layer and the substrate, constitutes the composite laminated structure of the present invention, which is intended to be provided with extensibility in designated selected zones 56 by means of mechanical straining preferably imparted by ring rolling.

The composite laminated structure according to the present invention eliminates the problems associated with built up of tacky adhesive on high speed straining equipment parts such as the rolls used for ring-rolling, together with the problem of the stiffness of the composite laminated structure that can lead to breaking of the adhesive layer and consequently at least partial delamination of the layers during the mechanical straining, preferably achieved by ring rolling.

In the preferred sanitary napkin/panty liner made according to the present invention shown in FIG. 2, the side wrapping elements each comprise composite laminate structures having two zones of extensibility 56 therein. The extensibility of all the zones of extensibility 56 on the side wrapping elements can be in the same direction. Alternatively, one or more of the zones of extensibility 56 may be extensible in a different direction. Also the extensibility in each zone 56 can vary if so desired.

The zones of extensibility 56 are preferably rendered capable of extending between 20% and 90%, more preferably between 50% and 80%, and most preferably between 70% and 80% under the forces associated with wearing the sanitary napkin in a pair of panties. The zones of extensibility 56 are also preferably extensible without being elastic. Further, any inherent elasticity in the zones of extensibility 56 (that is, any tendency of the material comprising the zones of extensibility to return to its original dimension) is generally relatively low to non-existent.

Composite Laminated Structure According to the Present Invention

The composite laminated structure according to the present invention comprises a substrate and an apertured layer, respectively corresponding to the microporous breathable film 3B and to the topsheet 2 in the preferred embodiment illustrated in FIGS. 1 and 2, and a layer of adhesive therebetween adhesively joining together the substrate and the apertured layer. The adhesive is considered useful to provide permanent adhesive connections between materials since the formed composite laminated structures typically have to be coherent.

By "adhesively joining" and "permanent adhesive connection", as used herein, it is meant that the adhesive should preferably withstand at least a peel strength of 0.4 N/2.5 cm. The peel strength is the strength required to peel apart the materials joined to each other on a sample strip of 2.5 cm width. A full test description is included in the following. The adhesive strength can of course exceed the material strengths of the materials joined. Therefore an alternative to the test against 0.4 N/2.5 cm can be the internal cohesion test. In this test an adhesive connection is delaminated. The adhesive connection satisfies the test if one of the materials is destroyed.

According to the present invention, the adhesive composition comprised in the composite laminated structure of the present invention has a peel force value on steel at a temperature of 23° C., indicative of a standard room temperature, of less than 10 g, preferably of less than 1 g, according to the Peel Force on Steel Test described in the following. This involves that when the composite laminated structure is subjected to mechanical straining, e.g. by means of ring rolling, and provided the temperature of the adhesive at this stage is the room temperature, therefore lower than the typical application temperature of the adhesive, machinery parts that come in direct contact with the adhesive layers through the apertures of the apertured layer during the mechanical straining, typically the apexes of the teeth of a roll for ring rolling, do not stick to the adhesive. This avoids adhesive build up on the machinery parts onto which the adhesive would otherwise adhere, and consequently pulling of the substrate layer through the apertures of the apertured layer by the roll teeth, with possible damage of the substrate itself.

In the preferred use of the composite laminated structure according to the present invention in the field of disposable absorbent articles such as sanitary napkins, another typically critical temperature is the body temperature of the wearer of disposable absorbent articles since any stickiness of the adhesive to the skin of the wearer could be also preferably prevented. Including a safety margin 40° C. is considered to be an adequate upper limit at which preferably the adhesive comprised in the composite laminated structure of the present invention should have a peel force on steel of less than 10 g, preferably less than 1 g.

As already mentioned a mechanical straining is applied to the composite laminated structure of the present invention in order to render designated selected zones of the structure extensible. As discussed above mechanical straining can be provided by any of the methods known in the art. However the most preferred method is ring rolling according to the above identified prior art publications. In the ring rolling step two rolls of meshed teeth and grooves interlock and thereby force material transported through the rolls to extend perpendicular to the groove direction.

The adhesive comprised in the composite laminated structure according to the present invention must have a low hardness and a sufficient extensibility to be able to withstand the mechanical straining process without breaking or in any case causing the layers of the composite laminated structure to delaminate. This requires that the adhesive composition used for the adhesive layer of the composite laminated structure of the present invention must have an elongation at break of at least 35%, preferably of at least 50%, as measured according to the Standard Test Method for Tensile Properties of Plastics ASTM D 638M-91a, wherein the thickness of the samples has the standard value of 4 mm. If the composite laminated structure of the present invention has to be mechanically strained by means of ring rolling, it is particularly preferred that the adhesive composition has an elongation at break at least equal to the highest strain which is induced in the composite laminated structure during the ring rolling, e.g. 100%.

Preferred adhesive compositions that can be comprised in the composite laminated structure of the present invention can be those described in our patent application entitled "Improved adhesive composition for a strainable composite laminated structure", filed on the same day of the present application (P&G case CM1886F). According to that disclosure, preferred adhesive compositions have a low viscosity at a relatively low application temperature, in order to make the application of the adhesive simple with the usual techniques employed with known hot melt adhesives, such as for example contact coating, roll coating, curtain coating, spraying, and moreover have a peel force value on steel at a temperature of 23° C. of less than 10 g, according to the same Peel Force Test described herein. Typically an adhesive composition according to that disclosure has a viscosity comprised between 1500 mPa.s and 10000 mPa.s at an application temperature in the range of 110° C. to 160° C., preferably lower than 5000 mPa.s at a temperature of not more than 160° C., more preferably comprised between 3000 mPa.s and 5000 mPa.s at a temperature of not more than 130° C.

Preferred adhesive compositions according to that application comprise, in weight percent, from 30% to 80% of a microcrystalline wax, from 5% to 70% of a polymer having an elongation at break of at least 400% according to ASTM D 638-91a, wherein the thickness of the samples has the standard value of 4 mm, and optionally up to 25% of a plasticising paraffinic oil. Preferably the adhesive composition comprises from 30% to 70%, preferably from 40% to 60% by weight of the microcrystalline wax, and from 30% to 70% by weight of the polymer, wherein the polymer is a copolymer of ethylene and vinyl acetate having a melt flow index (M.F.I.), evaluated by the ASTM method D 1238-85 under conditions 190/2.16, of at least 150 g/10 min, and a vinyl acetate content of at least 14% by weight. More preferably the polymer is a terpolymer also containing an acid monomer, e.g. acrylic acid, in an amount such that the acid number of the polymer is comprised between 1 and 100 mg of KOH per gram of the polymer.

Alternatively the adhesive composition according to the above mentioned application comprises, in weight percent, from 50% to 80% of the microcrystalline wax, and from 5% to 25% of the polymer having an elongation at break of at least 400% according to ASTM D 638-91a as defined above, wherein the polymer is a styrenic block copolymer having a styrene content comprised between 14% and 35% by weight.

Preferred optional components in the adhesive compositions according to the above mentioned application are up to 10% by weight of a paraffinic wax, or a mixture of paraffinic waxes, up to 25% by weight of an atactic poly-alpha-olefin, or of a mixture of atactic poly-alpha-olefins, and up to 40% by weight of a tackifying resin or blend of tackifying resins. Preferred tackifying resins are hydrocarbon resins, aliphatic, or aromatic, or aliphatic-aromatic resins, partially or fully hydrogenated resins, or mixtures thereof, wherein the resin or mixture of resins preferably have a softening point not higher than 100° C.

The adhesive composition to be included in the composite laminated structure of the present invention can also have the characteristics of a solder material as those disclosed in the two prior art publications EP-A-707841 and EP-A-710470 mentioned above, provided it also has the required elongation at break.

Joining materials by soldering requires to apply a solder to one or both surfaces to be joined and bringing the surfaces into contact before the solder cools below its solidifying temperature. In order to apply the solder it is heated to a temperature above its solidifying temperature and applied in a similar fashion or the same fashion as adhesives are applied. As a matter of fact the same equipment used today for applying adhesives can be adapted to apply the solder to the respective surface where it is needed. Methods like contact coating, roll coating, coating by spraying in random or designed patterns (such as swirl coating,) can all be used to apply the solder according to the present invention.

When bringing the surfaces to be joined together the solder contacts both surfaces intimately at a temperature above its solidifying temperature. It creates a permanent connection after cooling below the solidifying temperature. Incorporated within the word soldering according to the present invention are methods which in the metal art are referred to as brazing where the solder forms intermaterial bonds across the contact surface. While not wishing to be limited by theory it is believed that the solder forms a thin layer of intermaterial connections where the top molecular layers of the materials to be soldered to each other are involved. In order to distinguish a solder from generic adhesives a stickiness test for defining a solder is described in the already mentioned patent application EP-A-710470.

During the mechanical straining, preferably applied by ring rolling, of the composite laminated structure of the present invention, the breaking of the adhesive layer joining the substrate and the apertured layer is prevented by the extensibility of the adhesive composition. The adhesive build up on machinery parts that come into direct contact with the adhesive layer through the apertures of the apertured layer, and possible pulling of the substrate due to this effect, is on the other hand avoided due to the non stickiness of the adhesive to steel at room temperature.

In principle selective adhesive materials which are non-sticky in conjunction with steel but sticky on "other" surfaces are contemplated according to the present invention. Of course it is preferred that an adhesive used in a composite laminated structure according to the present invention is non sticky at room temperature on any material.

Further, not all material layers comprised in composite laminated structures according to the present invention undergoing mechanical straining, but excluding of course the adhesive layer, need to be strainable. By "strainable" it is meant that the material undergoes permanent deformation without destruction of its integrity. However the combination of non-strainable with strainable material can be strained. For example non-strainable nonwoven with strainable polymeric film, joined by an adhesive having the required extensibility in terms of elongation at break, could be strained. In this case the film is permanently deformed (and provides the desired zone of extensibility) while the non-woven would be locally destroyed (fibres or fibre bonds breaking) but otherwise remain firmly adhered to the film owing to the extensibility of the adhesive that does not ruptures under mechanical straining.

Test Methods

All tests conducted in respect to the present invention require test conditions of 23° C. plus minus 1° C. and relative humidity of 50% unless stated otherwise. Unless stated otherwise, all test materials are conditioned at this temperature and humidity for at least 4 hours prior to the test itself. Each result is averaged on ten test samples.

Peel Force Test

The peel force or peel strength test analyses the force required to delaminate a connection between materials when one material is peeled from the other material at a 180 degree angle according to the standard test method ASTM D 1876-72, but with a head speed of the tension testing machine of 100 mm/min. In respect to defining a permanent connection it has been found most sensible to create a realistic sample of the composite laminated structure of the present invention joined by an adhesive layer and analyse the peel strength between the actual materials to be joined to each other rather than attempt to standardise the materials or adhesive application. The test is conducted on a sample strip of 2.5 cm width having sufficient end tabs to apply the peel force equally across the whole width of the sample to be tested.

The peel strength of a connection by means of an adhesive layer between materials forming a composite laminated structure according to the present invention is sufficient if the force required to delaminate the joined connection is at least 0.4 N/2.5 cm or if the connection can withstand holding a load of 0.4 N without delaminating.

As already indicated materials having a cohesive strength less than the required 0.4 N/2.5 cm are still considered permanently connected by an adhesive if the material experiences destructive failure rather than the adhesive connection. Obviously this test is substantially easier in executing than the force measurement of the peel strength. It can also be used on materials having higher cohesive strength than 0.4 N/2.5 cm provided one of the materials and not the adhesive connection is destroyed. Therefore in general destruction of one of the materials joined together implies that the adhesive connection was permanent.

Peel Force on Steel Test

The peel strength or peel force on steel test measures the stickiness onto a steel surface at 23° C., which is considered as a standard room temperature, of an adhesive to be comprised into a composite laminated structure according to the present invention. The measurement of the peel force is performed in the same way as in the peel strength or peel force method described above (peel force at 180 degrees with 100 mm/min head speed), but the samples are prepared and handled as described hereinafter.

The adhesive composition is applied onto a substrate according to the supplier instructions in an amount of 80 g/m$^2$. For the current test method it has been found that using a Nordson slot coater with a 50 mm wide nozzle available from a Nordson, Lüneburg, Germany is useful. The adhesive is applied for this test in a width of at least 2.5 cm full surface coating at a speed of the first substrate of at least 0.5 m/s relative to the coating equipment. Wider coatings are acceptable while coatings of smaller width or only fractions of the width being coated (e.g. by spiral coating) are non acceptable in the context of this test. Of course such coating patterns can be used for applying the adhesive in the particular application context according to the present invention. The length of the adhesive layer in the individual test sample should be not less than 10 cm. The test sample has a sufficient end tab to allow the application of the peel force equally across the whole width of the adhesive coating on the sample to be tested.

The substrate is constituted by a polyethylene terephthalate (PET) film having a thickness of between 20 and 30 µm. Typically the adhesives used in the context of the present invention are hot melt adhesive compositions that are applied in the molten state at the temperature according to the manufacturers. A polyethylene terephthalate film as a substrate is capable to withstand the application of these adhesives in a broad range of application temperatures, which is typical in the context of disposable absorbent articles.

After the adhesive has been applied to the substrate it is allowed if necessary to cool to the temperature at which measurements are to be taken, while ensuring that the open side of the sample remains untouched and is only exposed to clean air.

The substrate is then positioned onto a horizontal 5×15 cm steel plate having a smooth, flat surface, according to what is specified in ASTM D 3330, with the entire surface of the sample coated with the adhesive layer contacting the steel plate. A pressure is applied with a compression roll weighing 2000 g, rolled once over the entire length of the sample at a speed of 300 mm/min. After application of pressure the samples are left for 30 seconds.

The measurement of the peel force at 180 degrees is conducted as described above, with a head speed of 100 mm/min of the tension testing machine, with the steel plate connected to the fixed clamp and with the substrate connected to the moving clamp at its free end tab.

Since it is preferred that the peel force on steel is as low as possible, it is possible, with particularly preferred adhesives, that it is virtually zero. In this case no force measurement is detected during delamination, or, alternatively, the film substrate can delaminate from the steel plate under its own weight when the steel plate is positioned vertically to be connected to the fixed clamp of the dynamometer. It is considered that in such cases the adhesive satisfies the test.

Elongation at Break Test

The elongation at break is measured according to the Standard Test Method for Tensile Properties of Plastics ASTM D 638M-91a, wherein the specimens prepared for the test have a standard thickness of 4 mm.

EXAMPLES

Two composite laminated structures have been prepared both comprising as the substrate a microporous breathable polymeric film produced by Mitsui under the tradename Espoir Microporous PG-01 with a basis weight of 40 g/m$^2$, and as the apertured layer a three dimensional apertured polymeric film produced by Tredegar under the tradename Dri-Wave. The substrate and the apertured layer are joined together by means of a layer of an adhesive composition comprised therebetween and applied by curtain coating in an amount of 11 g/m$^2$.

In the reference sample the composite laminated structure comprises a layer of an adhesive composition designated Fuller HS350, available from the H.B. Fuller Company. The adhesive composition comprised in the composite laminated structure made according to the present invention has the following composition in weight percentages:

Elvax 4310 (ethylenevinylacetate terpolymer available from Dupont) 59.7%
Witcodur 236 (microcrystalline wax available from Witco company) 40%
Irganox 1010 (antioxidant available from Ciba Geigy) 0.03%

Both the composite laminated structure satisfy the Peel Force Test, and both the adhesive compositions show virtually no adhesion to steel at 23° C. (no peel force measured in the Peel Force on Steel Test).

The two composite laminated structures are subjected to a mechanical straining by means of ring rolling in order to be provided with a 75% extension. In the reference sample the adhesive layer breaks causing delamination of the composite laminated structure. The failure of the adhesive connection can be ascertained for example by performing a second Peel Force Test on the strained structure: the basic requirement of at least 0.4 N/2.5 cm peel force are not satisfied anymore. The structure made according to the present invention on the contrary shows a satisfactory resistance of the adhesive composition to the mechanical straining, and the effectiveness of the adhesive connection can be demonstrated by a second Peel Force Test on the strained structure, where the requirement of 0.4 N/2.5 cm peel force is satisfied.

What is claimed is:

1. A composite laminated structure comprising a substrate, an apertured layer bonded to said substrate, and a layer of an adhesive composition comprised therebetween and adhesively joining said substrate and said apertured layer, said composite laminated structure having designated zones rendered extensible by mechanical straining, said composite laminated structure characterized in that
said adhesive composition has a peel force value on steel at a temperature of 23° C. of less than 10 g according to the Peel Force on Steel Test described herein, and
said adhesive composition has an elongation at break of at least 35% according to ASTM D 638M-91a where the sample thickness is 4 mm.

2. A composite laminated structure according to claim 1, wherein the peel force required to peel apart said substrate and said apertured layer on a sample strip 2.5 cm wide is at least 0.4 N.

3. A composite laminated structure according to claim 1, wherein peeling apart said substrate and said apertured layer either said substrate or said apertured layer is destroyed.

4. A composite laminated structure according to claim 1, wherein said adhesive composition has a peel force value on steel at a temperature of 23° C. of less than 1 g according to the Peel Force on Steel Test described herein.

5. A composite laminated structure according to claim 1, wherein said substrate is a breathable microporous film comprising a mixture of a thermoplastic polymer and particles of an inorganic filler.

6. A composite laminated structure according to claim 1, wherein said apertured layer is a thermoplastic three dimensional apertured polymeric film.

7. A composite laminated structure according to claim 1, wherein said predetermined extensibility is provided by means of a ring rolling process.

8. A disposable absorbent article comprising a composite laminated structure according to claim 1, wherein said substrate is a liquid impervious backsheet, and said apertured layer is a liquid permeable topsheet.

9. A disposable absorbent article according to claim 8, wherein said backsheet is moisture vapour permeable.

10. A disposable article according to claim 8, wherein said disposable article is a sanitary napkin used in the crotch portion of an undergarment, said article having side flaps, said side flaps comprising said composite laminated structure and extending beyond and wrapping around the side edge of the crotch portion of said undergarment, said extensible zones in said composite laminated structure being located so as to allow said side flaps to conform to said side edges of said crotch portion of said undergarment.

11. A disposable absorbent article according to claim 10, wherein said disposable arbsorbent article is a panty liner.

* * * * *